United States Patent
Tu et al.

(10) Patent No.: US 10,093,636 B2
(45) Date of Patent: Oct. 9, 2018

(54) METHOD FOR SYNTHESIZING BIO-PLASTICIZERS USING ACIDIC IONIC LIQUIDS AS CATALYSTS

(71) Applicant: CPC Corporation Taiwan, Taipei (TW)

(72) Inventors: You-Liang Tu, Taipei (TW); Ya-Shiuan Lin, Taipei (TW); Ming-Tsang Tsai, Taipei (TW); Chiu-Ping Li, Taipei (TW); Jung-Chung Wu, Taipei (TW)

(73) Assignee: CPC CORPORATION, TAIWAN, Taipei (TW)

( * ) Notice: Subject to any disclaimer, the term of this patent is extended or adjusted under 35 U.S.C. 154(b) by 8 days.

(21) Appl. No.: 15/229,649

(22) Filed: Aug. 5, 2016

(65) Prior Publication Data
US 2018/0037561 A1     Feb. 8, 2018

(51) Int. Cl.
*C07D 301/12*     (2006.01)
*C08K 5/1515*     (2006.01)

(52) U.S. Cl.
CPC .......... *C07D 301/12* (2013.01); *C08K 5/1515* (2013.01)

(58) Field of Classification Search
CPC ............................ C07D 301/12; C08K 5/1515
USPC ........................................................ 549/531
See application file for complete search history.

(56) References Cited

FOREIGN PATENT DOCUMENTS

| CN | 101029177 A | 9/2007 |
|---|---|---|
| CN | 101284821 A | 10/2008 |
| CN | 100590188 C | 2/2010 |
| CN | 101885710 A | 11/2010 |
| CN | 102060812 A | 5/2011 |
| CN | 102489333 A | 6/2012 |
| CN | 102787007 A | 11/2012 |
| CN | 103113993 A | 5/2013 |
| CN | 104326911 A | 2/2015 |
| CN | 104327015 A | 2/2015 |
| CN | 104341297 A | 2/2015 |

OTHER PUBLICATIONS

Cai et al, Epoxidation of Unsaturated Fatty Acid Methyl Esters in the Presence of SO3H-functional Bronsted Acidic Ionic Liquid as Catalyst, Chinese Journal of Chemical Engineering, 2011, 19(1), p. 57-63.*

Zhang et al, A Bronsted acidic ionic liquid as an efficient environmentally benign catalyst for biodiesel synthesis from free fatty acids and alcohols, Bioresource Technology, 2009, 100, p. 4368-4373.*

* cited by examiner

*Primary Examiner* — Taylor V Oh
(74) *Attorney, Agent, or Firm* — Muncy, Geissler, Olds & Lowe, P.C.

(57) ABSTRACT

Synthesizing bio-plasticizers with acidic ionic liquids as catalysts. The acidic ionic liquids are Bronsted acidic ionic liquids, which are composed of alkyl sulfone pyridinium and strong Bronsted acid. Epoxidized fatty acid alkyl esters could be obtained via epoxidation of fatty acid alkyl esters using the acidic ionic liquids as catalysts. The epoxidized fatty acid alkyl esters perform well as bio-plasticizers, which could be substituted for phthalate ester plasticizers. The acidic ionic liquids catalysts provide good catalytic performance, are easy to separate, reusable, and may reduce corrosion of pipelines.

16 Claims, 2 Drawing Sheets

METHOD FOR SYNTHESIZING BIO-PLASTICIZERS USING ACIDIC IONIC LIQUIDS AS CATALYSTS

BACKGROUND OF THE INVENTION

1. Field of the Invention

The present disclosure is a method for synthesizing bio-plasticizers using acidic ionic liquids as catalysts, particularly a method to epoxidize fatty acid alkyl esters by using Bronsted acidic ionic liquids as catalysts.

2. Brief Description of the Prior Art

The plastic additive is an imperative annexing agent for plastic processing, and is also known as plasticizer, plastifiant or elasticizer for more flexibility of a material. Plasticizers common in the industry are phthalate ester plasticizers which account for 85% of total output. For more flexibility and viscosity, phthalate ester plasticizers can be added into PVC for manufacturing plastic wraps, tubes and coating materials on electric wires or cables. However, phthalate esters with short carbon chains are totally petrochemical products and both phthalate ester plasticizers and their metabolites in human bodies are environmental hormones with adverse effects on metabolism and reproductive function. To decrease carbon footprints and enhance sustainable development of the environment, more and more manufacturers have been devoting themselves to developing environment-friendly plasticizers as well as bio-plasticizers.

Based on raw material of vegetable oil, epoxidized vegetable-oil plasticizers with good stability are popular bio-plasticizers, but are still mixed with phthalate ester plasticizers in applications because of the defect of poor compatibility. Comparably, epoxidized fatty acid alkyl esters can be taken as substitutes of conventional plasticizers, without the drawbacks of epoxidized vegetable oil. Currently, epoxidized plasticizers are usually manufactured in a process in which epoxy groups are generated by peroxy acid and unsaturated double bonds with concentrated sulfuric acid added as a catalyst. However, final products must be rinsed with a great quantity of water because concentrated sulfuric acid as a catalyst cannot be removed easily after reactions. Moreover, a great number of liquid waste to be discharged have to be neutralized in advance, but can still cause problems such as corrosion in equipment or pipelines.

To solve the above-noted problems related to use of concentrated sulfuric acid, a method which is based on reactants of formic acid, without strong-acid catalysts, induces autocatalysis which lasts for a long period (Patent No. CN 100590188C). Sobczak et al. used transition-metal compounds as catalysts, for example, molybdena catalyst/cumene hydroperoxide (CHP) or molybdena catalyst/tert-butyl hydroperoxide (t-BuOOH) composite catalyst system, and unsaturated fatty acid in reactions at 80° C. for 140~280 minutes to epoxidize oleic acid successfully wherein selectivity of epoxidation on the basis of the Mo(O)2(SAP)(EtOH)/t-BuOOH system is 86.8% (J. M. Scobczak, J. J. Ziólkowski, Appl. Catal. A, 248 (2003) 261-268). Farias et al. employed the MoO2(acac)2/t-BuOOH catalyst system to epoxidize soybean oil in 2-hour reactions at 110° C. and derived selectivity of epoxidation of 77.2% (M. Farias, M. Martinelli, D. P. Bottega, Appl. Catal. A, 384 (2010) 213-219). There have been many researchers in the academic community or the industry developing manufacturing processes which depend on solid catalysts to epoxidize vegetable oil or Fatty Acid Methyl Ester (FAME), for example, solid acidic catalysts (Patent No. CN 102489333A; CN 103113993A; CN 104326911A), solid base catalysts (Patent No. CN 101029177A), composite sulfate catalysts (Patent No. CN 102060812A), magnetic solid acidic catalysts (Patent No. CN 101885710A), because of some advantages including less acidic liquid waste in epoxidation based on solid catalysts and easy separations between heterogeneous catalysts. However, some problems such as activity decline of solid catalysts and reactivation of solid catalysts to be reused are still unavoidable.

To correct the above drawbacks, researchers employed ionic liquids with advantages such as easy separation, reusability, less corrosion in pipelines, and properties of both solid catalysts and traditional liquid acids to catalyze epoxidation. Chen et al. synthesized epoxidized fatty acid esters and hydroxylated fatty acid esters by ionic liquids of sulfoalkyl imidazolium salt as catalysts, mixing epoxidized fatty acid esters, hydroxylated fatty acid esters and additives to derive stamping and drawing oil (Patent No. CN 102787007B). Shen et al. employed 1-dodecyl-3-methyl-imidazolium bromide and ammonium perrhenate ($NH_4ReO_4$) for preparation of hydrophobic rhenium ionic liquids which were taken as catalysts to derive epoxidized FAME (epoxy value=2.65~4.57) (Patent No. CN 104327015A). Shen et al. used ionic liquids with sulfonic groups and heteropoly acids as catalysts to derive epoxidized FAME and continuously added glycerin in reactions to synthesize bio-oil-based polyol (Patent No. CN 104341297A). Chen et al. chose tetrafluoroborate, alkyl quaternary ammonium and alkyl quaternary phosphonium (alkyl replacing pyridinium and imidazolium) to prepare ionic liquids which were further taken as catalysts to synthesize expoxidized fatty acid methyl esters (epoxy value=3.1~4.7) (Patent No. CN 101284821A).

SUMMARY OF THE INVENTION

A method for synthesizing bio-plasticizers using acidic ionic liquids as catalysts is provided. More specifically, a method is provided for preparation of bio-plasticizers based on epoxidized fatty acid alkyl esters by using acidic ionic liquids as catalysts, which catalyze unsaturated double bonds of fatty acid alkyl esters to synthesize epoxy groups. Epoxidized fatty acid alkyl esters are taken to be bio-plasticizers which are further mixed with polyvinyl chloride (PVC) and undergo a thermal compression process for fabrication of soft PVC.

In the present disclosure, acidic ionic liquids as catalysts, fatty acid alkyl esters, organic acids and hydrogen peroxide are used to prepare epoxidized fatty acid alkyl esters in a one-pot synthesis process without solvents in manufacturing, for a lower follow-up treatment cost. As catalysts, acidic ionic liquids have advantages such as easy separation, reusability, and less corrosion in pipelines.

In the present disclosure, fatty acid alkyl esters can be biodiesel (Fatty Acid Methyl Esters (FAME)) or unsaturated fatty acid esters, for example, oleates or linoleates. Biodiesel is manufactured with vegetable oil, animal oil or used edible oil in a transesterification process. Oleates (or linoleates) are prepared by oleic acid (or linoleic acid) along with alcohol in an esterification process. Organic acids in the present disclosure can be formic acid (preferred herein) or acetic acid or mixtures of formic acid and acetic acid. The concentration of hydrogen peroxide solutions is over 30%. Acidic ionic liquids as catalysts in the present disclosure are Bronsted acidic ionic liquids (Bronsted Acid IL) with alkyl sulfonic acid replacing amphoteric compounds of pyridinium and synthesizing Bronsted acid.

The method for preparation of bio-plasticizers by acidic ionic liquids, which features simplicity and water resistance, is available to aquiferous reactions such as esterification and epoxidation. There are many advantages to preparing epoxidized fatty acid alkyl esters by acidic ionic liquids as catalysts, such as high selectivity and productivity, easy post-treatment, and reduced manufacturing cost due to neutralization of products with low-concentration weak-base solutions. The reuse rate of acidic ionic liquids extracted from an aqueous layer, which is separated from an organic layer and further concentrated and dried, is over 95%. The prepared epoxidized fatty acid alkyl esters with the epoxy value of over 3.30 are mixed with PVC powders and undergo a thermal compression process to derive soft PVC specimens with physical properties better than those of DOP/PVC-based (dioctyl phthalate/PVC-based) specimens.

A method for synthesizing bio-plasticizers using acidic ionic liquids as catalysts in the present disclosure comprises steps as follows:

Bronsted acidic ionic liquids are synthesized with strong Bronsted acid and alkyl sulfonic acid, which replaces amphoteric compounds of pyridinium, wherein the molar ratio of alkyl sulfonic acid to strong Bronsted acid is between 1.0 and 1.5; Fatty acid alkyl esters, organic acids and Bronsted acidic ionic liquids, all of which are mixed pro rata, are heated to 50° C. and further mixed with hydrogen peroxide solutions instilled within 1 hour for development of reaction solutions, which are further heated to and kept at 50~100° C. for epoxidation in 0.5~5 hours. The molar ratio of fatty acid alkyl esters to organic acids to hydrogen peroxide is 1:0.2~1:0.2~5 and the weight of Bronsted acidic ionic liquids is 1~15% of the total weight of organic acids and hydrogen peroxide solutions; and The oil-phase solutions of the reaction solutions are separated from the aqueous-phase solutions and rinsed with lye and deionized water for preparation of epoxidized fatty acid esters after removal of water.

In a method for synthesizing bio-plasticizers using acidic ionic liquids as catalysts, the alkyl in alkyl sulfonic acid, which replaces amphoteric compounds of pyridinium, is $C_nH_{2n}$ (n: between 3 and 6).

In a method for synthesizing bio-plasticizers using acidic ionic liquids as catalysts, strong Bronsted acid is sulfuric acid or alkyl sulfonic acid.

In a method for synthesizing bio-plasticizers using acidic ionic liquids as catalysts, the molar ratio of alkyl sulfonic acid replacing amphoteric compounds of pyridinium in Bronsted acidic ionic liquids to strong Bronsted acid is further between 1.0 and 1.2.

In a method for synthesizing bio-plasticizers using acidic ionic liquids as catalysts, fatty acid alkyl esters are biodiesel, unsaturated fatty acid alkyl esters, or mixtures of biodiesel and unsaturated fatty acid esters. Biodiesel is Fatty Acid Methyl Esters (FAME) manufactured with vegetable oil, animal oil or used edible oil in a transesterification process. Unsaturated fatty acid alkyl esters are derived from unsaturated fatty acids and alcohols in an esterification process. Unsaturated fatty acid is oleic acid, linoleic acid, or a combination thereof. Alcohol is methanol, ethanol, propyl alcohol or butanol.

In a method for synthesizing bio-plasticizers using acidic ionic liquids as catalysts, time to epoxidize unsaturated fatty acid esters, biodiesel, and mixtures of biodiesel and unsaturated fatty acid alkyl esters is 3~5 hours, 0.5~1 hour, and 0.5~1 hour, respectively.

In a method for synthesizing bio-plasticizers using acidic ionic liquids as catalysts, organic acids are formic acid, acetic acid or a combination thereof.

In a method for synthesizing bio-plasticizers using acidic ionic liquids as catalysts, the concentration of hydrogen peroxide solutions is between 30 and 35 wt %.

In a method for synthesizing bio-plasticizers using acidic ionic liquids as catalysts, the molar ratio of fatty acid alkyl esters to organic acids is 1:0.2~1.0.

In a method for synthesizing bio-plasticizers using acidic ionic liquids as catalysts, the molar ratio of fatty acid alkyl esters to organic acids is further 1:0.5~0.8.

In a method for synthesizing bio-plasticizers using acidic ionic liquids as catalysts, the molar ratio of fatty acid alkyl esters to hydrogen peroxide solutions is 1:0.5~2.

In a method for synthesizing bio-plasticizers using acidic ionic liquids as catalysts, the molar ratio of fatty acid alkyl esters to hydrogen peroxide solutions is further 1:0.2~5.0.

In a method for synthesizing bio-plasticizers using acidic ionic liquids as catalysts, the weight of Bronsted acidic ionic liquids is further 5~10% of the total weight of organic acids and hydrogen peroxide solutions.

In a method for synthesizing bio-plasticizers using acidic ionic liquids as catalysts, the weight of Bronsted acidic ionic liquids is further 5~8% of the total weight of organic acids and hydrogen peroxide solutions.

In a method for synthesizing bio-plasticizers using acidic ionic liquids as catalysts, the temperature for epoxidation is between 55 and 85° C.

In a method for synthesizing bio-plasticizers using acidic ionic liquids as catalysts, the temperature for epoxidation is further between 70 and 85° C.

DETAILED DESCRIPTION OF THE PREFERRED EMBODIMENT

The molar ratio of fatty acid alkyl esters to organic acids to hydrogen peroxide is 1:0.3~1:1~2, the weight of added acidic ionic liquids is 5~8% of the total weight of organic acids and hydrogen peroxide, the reaction temperature is between 55 and 85° C., and the reaction time is between 0.5 and 5 hours.

Fatty acid alkyl esters, organic acids and acidic ionic liquids, all of which are added into a reactor pro rata, are heated to 50° C., agitated and mixed with hydrogen peroxide which is instilled appropriately within 1 hour. With hydrogen peroxide instilled completely, the temperature is increased to 55~85° C., kept for 0.5~5 hours, and followed by removal of the aqueous phase at the end of reaction. Epoxidized fatty acid alkyl esters are derived after oil-phase products are rinsed with lye and deionized water. The structure of epoxidized fatty acid alkyl esters is analyzed in the one-dimensional proton nuclear magnetic resonancespectrum, productivity, transformation rate and selectivity of epoxidized fatty acid alkyl esters are calculated, and the epoxy value is determined according to GB 1677-81 (hydrochloric acid-acetone method).

Figure 1:
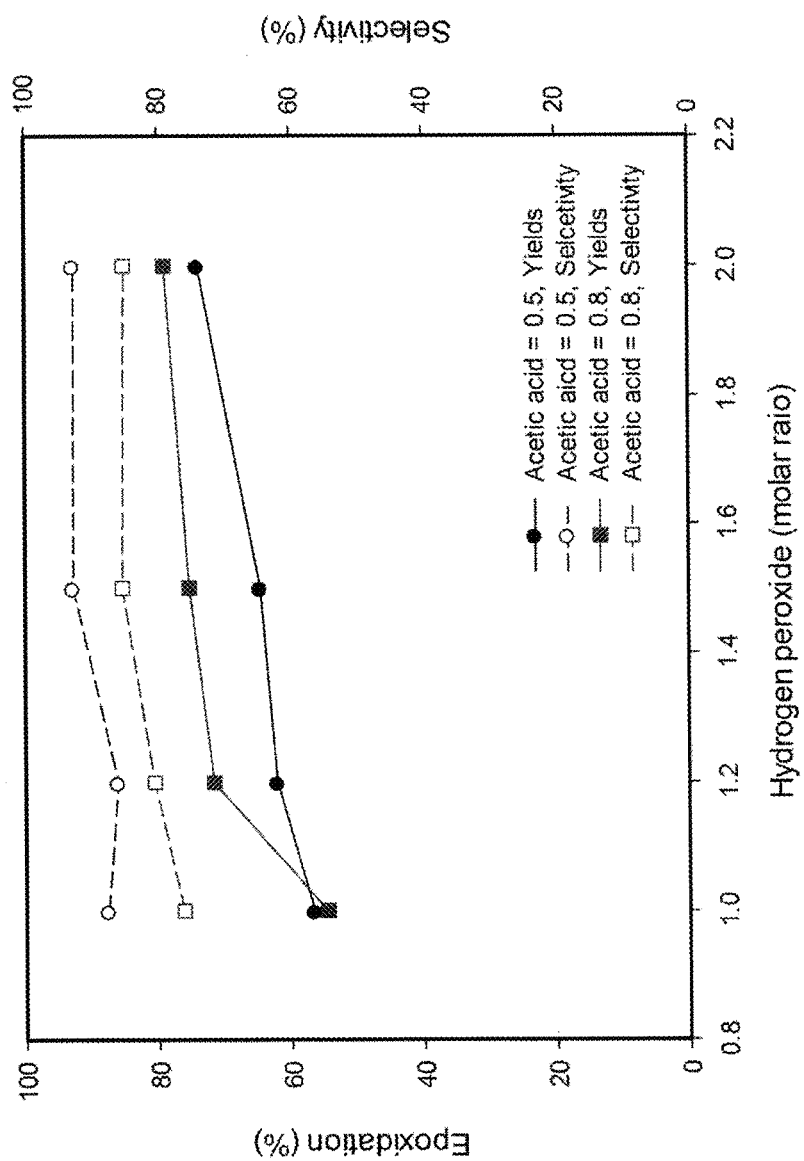
FIG. 1 illustrates productivity and selectivity of epoxidized oleates which are prepared with acetic acid and hydrogen peroxide in various proportions.

Embodiment 1: epoxidation based on acetic acid and hydrogen peroxide solutions in various proportions. Methyl oleate and acetic acid (the molar ratio of methyl oleate to acetic acid=1:0.5~0.8) are added into a reaction bottle, mixed with 8% acidic ionic liquids, and agitated and heated to 50° C. 30% hydrogen peroxide solutions (the mole of hydrogen peroxide is 1~2 times as many as that of methyl oleate) are controllably instilled in the reaction bottle within 1 hour and heated to 55° C. for generation of raw products in 5 hours. The raw products are kept at a standing condition for separation of the aqueous phase and the oil phase. The oil phase in the upper layer is rinsed with sodium bicarbonate solutions and deioned water to derive epoxidized oleates after removal of water. It can be seen from FIG. 1 that productivity of epoxidized oleates is up to 64.5~79% when the feeding ratio of hydrogen peroxide is kept at 1.5~2.

Figure 2:
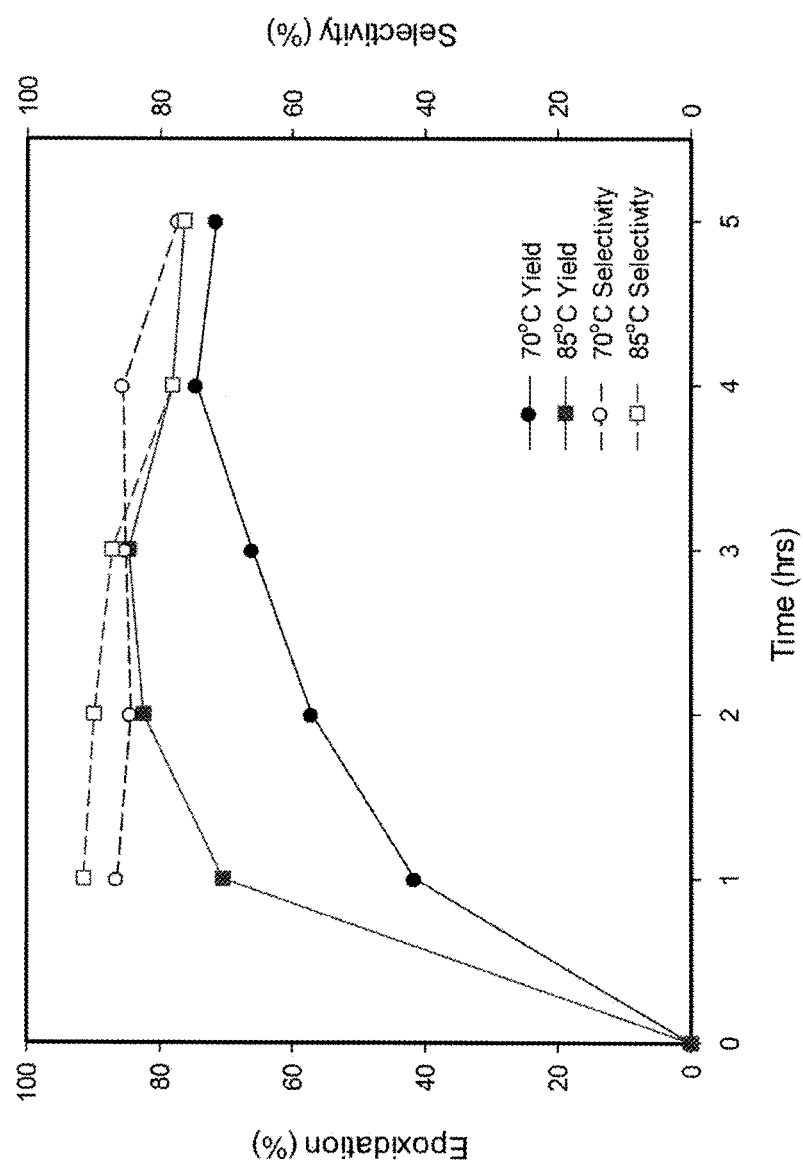
FIG. 2 illustrates productivity and selectivity of epoxidized oleates which are prepared in different reaction temperatures and durations.

Embodiment 2: epoxidation under same conditions (feeding ratio and temperature) and sampling analyses at distinct reaction time. Methyl oleate and acetic acid (the molar ratio of methyl oleate to acetic acid=1:0.5) are added into a reaction bottle, mixed with 8% acidic ionic liquids, and agitated and heated to 50° C. 30% hydrogen peroxide solutions (the mole of hydrogen peroxide is 1.5 times as many as that of methyl oleate) are controllably instilled in the reaction bottle within 1 hour and heated to 70~85° C. for generation of raw products in 1~5 hours. The raw products are kept at a standing condition for separation of the aqueous phase and the oil phase. The oil phase in the upper layer is rinsed with sodium bicarbonate solutions and deioned water to derive epoxidized oleates after removal of water. It can be seen from outcomes that both productivity and selectivity of epoxidized oleates in longer reaction time are decreased. As shown in FIG. 2, productivity of epoxidized oleates is 74.5% (reaction temperature: 70° C.; best reaction time: 4 hours) and 84.8% (reaction temperature: 85° C.; best reaction time: 3 hours), respectively.

Embodiment 3: epoxidation catalyzed with acidic ionic liquids in various proportions. Methyl oleate and acetic acid (the molar ratio of methyl oleate to acetic acid=1:0.5~0.8) are added into a reaction bottle, mixed with 5~8% acidic ionic liquids, and agitated and heated to 50° C. 30% hydrogen peroxide solutions (the mole of hydrogen peroxide is 1.2~1.5 times as many as that of methyl oleate) are controllably instilled in the reaction bottle within 1 hour and heated to 55° C. for generation of raw products in 5 hours. The raw products are kept at a standing condition for separation of the aqueous phase and the oil phase. The oil phase in the upper layer is rinsed with sodium bicarbonate solutions and deioned water to derive epoxidized methyl oleates after removal of water. It can be seen from Table 1 that productivity and selectivity of epoxidized methyl oleates with 8% acidic ionic liquids as catalysts added are over 70% and 85%, respectively.

Table 1, transformation rate, productivity and selectivity of epoxidized methyl oleates with catalysts in various proportions added

| Sample ID | Ester:organic acid:hydrogen peroxide (molar ratio) | Percentage of catalysts (%) | Transformation rate (%) | Productivity (%) | Selectivity (%) |
|---|---|---|---|---|---|
| 1 | 1:0.5:1.5 | 5 | 69.5 | 64.5 | 92.8 |
| 2 | 1:0.5:1.5 | 8 | 79.3 | 74.1 | 93.4 |
| 3 | 1:0.8:1.2 | 5 | 69.5 | 56.0 | 80.6 |
| 4 | 1:0.8:1.2 | 8 | 81.7 | 71.5 | 87.6 |
| 5 | 1:0.8:1.5 | 5 | 83.7 | 72.6 | 86.7 |
| 6 | 1:0.8:1.5 | 8 | 88.2 | 75.3 | 85.4 |

Embodiment 4: epoxidation based on different organic acids and sampling analyses at distinct reaction time. Biodiesel and formic acid or acetic acid (the molar ratio of biodiesel to formic acid (or acetic acid)=1:0.5) are added into a reaction bottle, mixed with 8% acidic ionic liquids, and agitated and heated to 50° C. 30% hydrogen peroxide solutions (the mole of hydrogen peroxide is twice as many as that of methyl oleate) are controllably instilled in the reaction bottle within 1 hour and heated to 70° C. for generation of raw products in 0.5~2 hours. The raw products are kept at a standing condition for separation of the aqueous phase and the oil phase. The oil phase in the upper layer is rinsed with sodium carbonate solutions and water to derive expoxidized fatty acid methyl esters after removal of water. It can be seen from Table 2 that formic acid performs better than acetic acid. Productivity of expoxidized fatty acid methyl esters and the epoxy value with formic acid employed in same conditions are over 65% and 4.65, respectively. Productivity of expoxidized fatty acid methyl esters and the epoxy value with acetic acid employed in same conditions are 45% and 3.43, respectively.

Table 2, transformation rate, productivity, selectivity and epoxy value of expoxidized fatty acid methyl esters in distinct reaction time with organic acids added

| Sample ID | Organic acid | Reaction time (hr) | Transformation rate (%) | Productivity (%) | Selectivity (%) | Epoxy value |
|---|---|---|---|---|---|---|
| 1 | acetic acid | 0.5 | 63.1 | 48.4 | 76.7 | 3.30 |
| 2 | acetic acid | 1 | 57.3 | 44.9 | 78.5 | 3.32 |
| 3 | acetic acid | 2 | 63.8 | 45.2 | 70.9 | 3.43 |
| 4 | formic acid | 0.5 | 76.9 | 65.4 | 85.0 | 4.77 |
| 5 | formic acid | 1 | 83.0 | 66.4 | 80.0 | 4.65 |

Embodiment 5: epoxidation catalyzed with acidic ionic liquids and tests of reuse rates. Biodiesel and formic acid (the molar ratio of biodiesel to formic acid=1:0.5) are added into a reaction bottle, mixed with 8% acidic ionic liquids, and agitated and heated to 50° C. 30% hydrogen peroxide solutions (the mole of hydrogen peroxide is twice as many as that of methyl oleate) are controllably instilled in the reaction bottle within 1 hour and heated to 70° C. for generation of raw products in 0.5 hour. The raw products are kept at a standing condition for separation of the aqueous phase and the oil phase. The oil phase in the upper layer is rinsed with sodium carbonate solutions and water to derive expoxidized fatty acid methyl esters after removal of water. The aqueous phase in the lowered layer is concentrated and dried in vacuum to derive acidic ionic liquids which are further recycled and reused in epoxidation under preceding experimental conditions. It can be seen from outcomes that productivity of expoxidized fatty acid methyl esters and the epoxy value with acidic ionic liquids reused in the third time are 61.8% and 4.58, respectively. In summary, acidic ionic liquids with the reuse rate of over 95% are verified as recycled and reused substances.

Embodiment 6: PVC powders and epoxidated fatty acid esters as plasticizers are mixed and conglomerated at 170° C. in 5~15 minutes and undergo a 2-minute thermal compression process at 180° C. and a 3-minute cold compression process to form PVC specimens which are further tested for maximum tensile strength, elongation at break, and hardness, compared with specimens of the control group based on dioctyl phthalate (DOP, phthalate ester plasticizers), and formed in the same conditions such as proportions of ingredients, mixing and thermal compression. It can be seen from Table 3 that epoxidized fatty acid esters, which surpass DOP in elongation at break (>250%), Shore D (≤35) and tensile strength (200~240 kgf/cm$^2$) with plasticizers (30 wt %) added in reactions, are taken as bio-plasticizers replacing DOP. For raw materials in reactions, the weight percentage of S-80 PVC powders manufactured in Formosa Plastics Corporation is 70 wt %. Calcium-zinc stabilizers (5 phr) are added into plasticizers and PVC powders for mixing. The epoxy values of plasticizers are tested according to GB 1677-81 (hydrochloric acid-acetone method). The tensile tests are conducted according to ASTM D368—Standard Test Method for Specific Gravity of Creosote and Oil-Type Preservatives. The harness tests are conducted according to ASTM D2240—Standard Test Method for Rubber Property—Durometer Hardness.

Table 3, physical property tests on PVC specimens prepared with expoxidized fatty acid methyl esters as plasticizers

| No. | Plasticizers/weight percentage | Epoxy value | Tensile strength (kgf/cm$^2$) | Elongation at break (%) | Hardness Shore D |
|---|---|---|---|---|---|
| 00 | DOP/30 wt % | N/A | 246 | 248 | 47 |
| 01 | Epoxidized methyl oleate/30 wt % | 4.05 | 200 | 274 | 35 |
| 02 | Expoxidized fatty acid methyl ester/30 wt % | 3.30 | 203 | 253 | 34 |
| 03 | Expoxidized fatty acid methyl ester/30 wt % | 3.43 | 224 | 266 | 34 |
| 04 | Expoxidized fatty acid methyl ester/30 wt % | 4.65 | 230 | 292 | 32 |
| 05 | Expoxidized fatty acid methyl ester/30 wt % | 4.77 | 240 | 305 | 31 |

What is claimed is:

1. A method for synthesizing bio-plasticizers using acidic ionic liquids as catalysts, comprising the following steps:
    synthesizing Bronsted acidic ionic liquids with a strong Bronsted acid and an alkyl sulfonic acid, which replaces amphoteric compounds of pyridinium, wherein a molar ratio of the alkyl sulfonic acid to the strong Bronsted acid is between 1.0 and 1.5;
    heating fatty acid alkyl esters, organic acids and Bronsted acidic ionic liquids, all of which have been mixed pro rata, to 50° C. and further mixing in hydrogen peroxide solutions instilled within 1 hour, for development of reaction solutions, then further heating the resulting mixture to a temperature of 50-100° C. for epoxidation and maintaining the epoxidation temperature for 0.5-5 hours, wherein a molar ratio of fatty acid alkyl esters to organic acids to hydrogen peroxide is 1:0.2-1:0.2-5, and a weight of Bronsted acidic ionic liquids is 1-15% of the total weight of organic acids and hydrogen peroxide solutions; and
    separating oil-phase solutions of the reaction solutions from aqueous-phase solutions and rinsing the oil-phase solutions with lye and deionized water for preparation of epoxidized fatty acid esters after removal of water,
    wherein the Bronsted acidic ionic liquids are reused at least 10 cycles and the catalytic efficiency is more than 95% in each cycle, and
    wherein the productivity of the oleates based on the method is up to 85%.

2. The method for synthesizing bio-plasticizers using acidic ionic liquids as catalysts as claimed in claim 1, wherein the alkyl in the alkyl sulfonic acid, which replaces amphoteric compounds of pyridinium, is $C_nH_{2n}$, n is between 3 and 6.

3. The method for synthesizing bio-plasticizers using acidic ionic liquids as catalysts as claimed in claim 1, wherein the strong Bronsted acid is sulfuric acid or alkyl sulfonic acid.

4. The method for synthesizing bio-plasticizers using acidic ionic liquids as catalysts as claimed in claim, 1 wherein the molar ratio of the alkyl sulfonic acid, which replaces amphoteric compounds of pyridinium in Bronsted acidic ionic liquids, to the strong Bronsted acid is further between 1.0 and 1.2.

5. The method for synthesizing bio-plasticizers using acidic ionic liquids as catalysts as claimed in claim 1, wherein: the fatty acid alkyl esters are biodiesel, unsaturated fatty acid alkyl esters, or mixtures of biodiesel and unsaturated fatty acid esters; the biodiesel is Fatty Acid Methyl Esters (FAME) manufactured with vegetable oil, animal oil or used edible oil in a transesterification process; the unsaturated fatty acid alkyl esters are derived from unsaturated fatty acids and alcohols in an esterification process; the unsaturated fatty acid is oleic acid, linoleic acid, or a combination thereof; and the alcohol is methanol, ethanol, propyl alcohol or butanol.

6. The method for synthesizing bio-plasticizers using acidic ionic liquids as catalysts as claimed in claim 5, wherein a time to epoxidize unsaturated fatty acid esters is 3-5 hours, a time to epoxidize biodiesel is 0.5-1 hours, and a time to epoxidize mixtures of biodiesel and unsaturated fatty acid alkyl esters is 0.5-1 hour.

7. The method for synthesizing bio-plasticizers using acidic ionic liquids as catalysts as claimed in claim 1, wherein the organic acids are formic acid, acetic acid or a combination thereof.

8. The method for synthesizing bio-plasticizers using acidic ionic liquids as catalysts as claimed in claim 1, wherein a concentration of hydrogen peroxide solutions is between 30 and 35 wt %.

9. The method for synthesizing bio-plasticizers using acidic ionic liquids as catalysts as claimed in claim 1, wherein the molar ratio of fatty acid alkyl esters to organic acids is 1:0.2-1.0.

10. The method for synthesizing bio-plasticizers using acidic ionic liquids as catalysts as claimed in claim 9, wherein the molar ratio of fatty acid alkyl esters to organic acids is further 1:0.5-0.8.

11. The method for synthesizing bio-plasticizers using acidic ionic liquids as catalysts as claimed in claim 1, wherein a molar ratio of fatty acid alkyl esters to hydrogen peroxide solutions is 1:0.5-2.

12. The method for synthesizing bio-plasticizers using acidic ionic liquids as catalysts as claimed in claim 11, wherein the molar ratio of fatty acid alkyl esters to hydrogen peroxide solutions is further 1:0.2-5.0.

13. The method for synthesizing bio-plasticizers using acidic ionic liquids as catalysts as claimed in claim 1, wherein the weight of Bronsted acidic ionic liquids is further 5-10% of the total weight of organic acids and hydrogen peroxide solutions.

14. The method for synthesizing bio-plasticizers using acidic ionic liquids as catalysts as claimed in claim 13, wherein the weight of Bronsted acidic ionic liquids is further 5-8% of the total weight of organic acids and hydrogen peroxide solutions.

15. The method for synthesizing bio-plasticizers using acidic ionic liquids as catalysts as claimed in claim 1, wherein the temperature for epoxidation is between 55and 85° C.

16. The method for synthesizing bio-plasticizers using acidic ionic liquids as catalysts as claimed in claim 15, wherein the temperature for epoxidation is further between 70 and 85° C.

\* \* \* \* \*